United States Patent [19]  [11] 4,075,231
Dolhyj et al.  [45] Feb. 21, 1978

[54] PROCESS FOR PREPARING PHTHALIC ANHYDRIDE

[75] Inventors: Serge R. Dolhyj, Parma; Ernest C. Milberger, Solon; James F. White, Akron, all of Ohio

[73] Assignee: The Standard Oil Company, Cleveland, Ohio

[21] Appl. No.: 741,174

[22] Filed: Nov. 12, 1976

Related U.S. Application Data

[63] Continuation-in-part of Ser. No. 572,260, April 28, 1975, abandoned, which is a continuation of Ser. No. 362,412, May 21, 1973, abandoned.

[51] Int. Cl.$^2$ ............................................. C07D 307/89
[52] U.S. Cl. ................................. 260/346.4; 252/432; 252/461; 252/477 R
[58] Field of Search ..................................... 260/346.4

[56] References Cited

U.S. PATENT DOCUMENTS

| 2,954,385 | 9/1960 | Burney et al. .................... 260/346.4 |
| 3,464,930 | 9/1969 | Friedrichsen et al. .......... 252/461 X |

FOREIGN PATENT DOCUMENTS

1,011,678  12/1965  United Kingdom.

Primary Examiner—Richard L. Raymond
Attorney, Agent, or Firm—Gwenetta Douglas Hill; Herbert D. Knudsen; Larry W. Evans

[57] ABSTRACT

Phthalic anhydride is prepared by the oxidation of ortho-xylene with molecular oxygen at a temperature of about 200° to about 600° C. in the presence of an oxidation catalyst that comprises an essentially inert support having a strongly-adhering coat of a catalytic composition containing an oxide of vanadium wherein the concentration of vanadium is less than 10%.

17 Claims, No Drawings

PROCESS FOR PREPARING PHTHALIC ANHYDRIDE

REFERENCE TO RELATED APPLICATIONS

This is a continuation-in-part to our earlier application, Ser. No. 572,260, filed Apr. 28, 1975, now abandoned, which is a continuation of Ser. No. 362,412, filed May 21, 1973, now abandoned.

BACKGROUND OF THE INVENTION

The oxidation of ortho-xylene to phthalic anhydride is known. The reactant ratios, conditions and other parameters shown in the art are substantially unchanged. The present invention is the discovery of a particular group of catalysts that are especially effective in this reaction. The catalysts are very easy to prepare; they give smooth temperature control and high per pass conversions.

U.S. Pat. No. 3,464,930 discloses use of a catalyst containing vanadium and titanium coated on nonporous, inert materials, i.e., materials free from pores or having a small surface area, preferably less than 3 sq. m./g. This patent discloses the preparation of a catalyst containing the oxides of titanium and vanadium by pretreating a carrier of fused aluminum oxide with titanium tetrachloride and glacial acetic acid and bringing this carrier in contact with a paste comprising vanadium oxalate and anatase.

British Pat. No. 1,140,264 is an equivalent of U.S. Pat. No. 3,464,930.

British Pat. No. 1,203,321, a Patent of Addition to No. 1,140,264, discloses oxidation catalysts which are an improvement over the oxidation catalysts containing vanadium pentoxide and titanium dioxide in British Pat. No. 1,140,264. British Pat. No. 1,203,321 discloses that the coating on catalysts which have been coated with the composition containing vanadium pentoxide and titanium dioxide by applying the composition in a dissolved or suspended form to a carrier which has been heated to a temperature of 160° to 500° C. has greater strength. The object of this invention is to overcome the disadvantage in British Pat. No. 1,140,264 of resistance to abrasion.

British Pat. No. 1,237,954 discloses the air oxidation of o-xylene in a tubular reactor at an elevated temperature in contact with a fixed-bed catalyst comprising a nonporous carrier having a coating of a composition containing vanadium oxide and titanium oxide. The object of this invention is to overcome the disadvantage of catalyst discoloration in British Pat. No. 1,140,264.

British Pat. No. 1,238,379 discloses use of supported catalysts containing titanium dioxide, vanadium pentoxide and aluminum oxide, lithium oxide and/or zirconium dioxide coated on an inert nonporous carrier. The object of this invention is to overcome the disadvantage in British Pat. No. 1,140,264, wherein the catalyst does not achieve their optimum effect until after a certain operational period.

British Pat. No. 1,267,043 discloses the use of catalysts containing vanadium pentoxide, titanium dioxide and a phosphorus compound coated on nonporous inert carriers. The object of this invention is to improve the life of catalysts such as those described in British Pat. No. 1,140,264.

Only unexpected results are obtained using novel catalysts of the invention for the production of phthalic anhydride.

SUMMARY OF THE INVENTION

The present invention is the discovery of particular catalysts that are especially effective in the oxidation of ortho-xylene to phthalic anhydride. In the process for preparing phthalic anhydride by contacting a mixture of ortho-xylene and molecular oxygen at a temperature of about 200° to about 600° C. in the presence of an oxidation catalyst which is useful for reaction in a fixed-bed reactor, the reaction is improved by using an oxidation catalyst comprising (a) an essentially inert, porous support having a particle size of at least about 20 microns, said inert support having an outer surface; and (b) a coating of a catalytically active oxide material on said outer surface of said support which strongly adheres to said outer surface of said inert support, said catalytically active material containing boron, antimony or mixture thereof and an oxide of vanadium such that the weight of vanadium is less than 10% of the total weight of the oxidation catalyst. The catalysts of the present invention give a controllable reaction with high per pass conversions to phthalic anhydride and desirably low amounts of useless byproducts. The catalysts are also especially easy to prepare and are attrition resistant.

As noted, the focal point of the present invention is the use of a new catalyst in the known oxidation of ortho-xylene. The catalyst gives especially good results in the reaction.

The special coated catalyst consists of an inner-support material having an outer surface and a uniform coating of the active catalytic material on this outer surface.

The essentially inert support can be selected from any material that is at least partially porous and that has the physical integrity to withstand the catalyst preparation techniques and the conditions of the oxidation reaction. The porosity is required for the preparation of the catalyst, and the stability of the support is required for the attrition resistance.

By the preferred procedure of the invention, the support material employed is porous. By this is meant the support material must be susceptible to the penetration of liquid. Preferred support materials are capable of absorbing at least 1% by weight water based upon the weight of the support.

Suitable materials that are among the inert supports include silica, Alundum, alumina, alumina-silica, silicon carbide, titania and zirconia. This list is representative of those materials that can be used. Of course, many other materials having the attributes discussed above could be substituted for these support materials.

As noted in the broad description of the invention, the inert support is at least 20 microns in size. There is no theoretical upper limit to the size of the inert support, but for practical reasons, the support is normally not larger than about 5 centimeters. Preferred supports are about 0.2 cm. to about 2 cm.

The shape of the inert support may vary widely. Irregular or regular shapes may be used, and in the preferred practice of the invention, spherical supports are employed.

Having described the inert support component of the catalyst, the active catalytic material will be described. As noted, the active ingredients contain at least an oxide of vanadium. Broadly preferred in the present invention is vanadium pentoxide that has been partially reduced with a reducing agent so that at least some of the vanadium is present at a lower valence state than +5.

The partial reduction of the vanadium in the catalyst is conveniently accomplished by reducing vanadium pentoxide with a suitable reducing agent. Representative examples of reducing agents include: organic reducing agents, such as hydrazine, or finely divided metals, such as tungsten or molybdenum.

Specific catalyst compositions of special interest are described by the formula $$A_a D_b V_{12} O_x$$

wherein

A is Fe, Cr, Ni, Co, Mn, Cu, Ag, Bi, Zn, Mo, W or mixture thereof;
D is B, Sb or mixture thereof;
$a$ is a number from greater than 0 to 5;
$b$ is a number from greater than 0 to 10; and
$x$ is the number of oxygens required to satisfy the valence requirements of the other elements present.

Of these catalysts, those containing a mixture of boron and antimony are preferred. Most preferred are those wherein $b$ is a number from greater than 0 to 5. Also preferred are catalysts wherein A is a metal selected from molybdenum or tungsten.

A very important aspect of the present invention is that the weight of vanadium in the catalyst is less than about 10% by weight of the entire catalyst. Preferred are catalysts that contain less than 5 percent vanadium, with the best results being obtained with those catalysts containing less than one percent vanadium.

Even though the vanadium oxide could be placed on the inert support as the pure oxide, it is preferred to mix the active catalytic ingredients with a solid diluent prior to coating the inert support. Such solid diluents may conveniently be any of the support materials used or any other solid diluent. Preferred solid diluents are titanium dioxide, silica or mixture thereof. The solid diluent may be combined with the active ingredients in any combination that will give the desired catalyst. Most preferred are catalysts employing a solid diluent and containing less than about 0.5% by weight of vanadium. Especially preferred catalysts contain active catalytic ingredients of boron, antimony and an oxide of vanadium mixed with titanium dioxide, or catalysts containing active catalytic ingredients of boron, and an oxide of vanadium mixed with titanium dioxide.

The total coated catalyst of the present invention is conveniently prepared by partially wetting the inert support with a liquid such as water. This partially wet support should contain some liquid, but there should be no surface liquid visible. The support should not be wet on the outer surface of the total mass. It should be dry to the touch. The partially wet support is contacted with a powder of the active ingredient composition, and the inert support is rolled in the active ingredients. The contact between the powder and inert support is easily accomplished by placing the support in a closed container, rotating the container in an inclined plane and adding portions of the powder. Preferably, substantially all of one portion of the powder is coated on the support before another portion is added.

By the preferred procedure of the invention, the catalyst is prepared by contacting an essentially inert, at least partially porous support of at least 20 microns in diameter with a measured amount of liquid to produce a partially wet support, said support being one that does not have the appearance of having liquid on the outer surface of the support, but has at least some liquid absorbed on the support, and (2) rolling the support in a powder of the catalytically active material to produce a support having a hard uniform coating of the catalytically active material on the outer surface of the support.

The catalysts prepared by this process consist of the inert support and a strongly-adhering coat of the active catalytic ingredients on the outer surface of the support. The catalytic ingredients are maintained on the surface of the support, and there is essentially no impregnation of the active ingredients into the inert support. Thus, the catalysts of the invention are sharply contrasted with those catalyst techniques that impregnate an inert support with an active catalyst by contacting the support with a liquid or slurry of active ingredients.

The coated catalyst of the present invention is used in the oxidation of ortho-xylene to phthalic anhydride. This oxidation is a known reaction, and the reaction conditions, feed ratios and design of the reaction system is not materially changed from that of the art. Broadly, the ratio of molecular oxygen to ortho-xylene could be as low as about four moles per mole of xylene, but there is no theoretical upper limit. Normally, the molecular oxygen is added as air, and the air/xylene ratio usually ranges from about 40 to 130 or more.

The reaction temperature may vary widely but is usually within the range of about 200° to about 600° C, with temperature of about 300° to 500° C. being preferred. The reaction can be run at atmospheric, superatmospheric or subatmospheric pressure. The catalysts of the invention are most suited for fixed-bed operation, but using small support particles, it is also possible to conduct the reaction in a fluid-bed reactor.

The catalysts of the invention produce especially high yields of phthalic anhydride and useful by-products. The oxidation reaction, using the catalysts of the invention, is also easy to control. In the past, the exotherm created in the reactor caused loss of control, but now with the catalysts of the invention, an even temperature is easily maintained without use of special diluents or low reactant feed rates.

SPECIFIC EMBODIMENTS

EXAMPLES 1-11

Preparation of Phthalic Anhydride Using Coated Catalysts of the Invention

Various catalysts of the invention were prepared as described below. A catalytic reactor having a reaction zone of 20 cc. was constructed from a 1.02 cm. inside diameter stainless steel tube. The reactor was maintained in a metal block furnace, and a thermocouple was placed inside of the catalytic bed. Ortho-xylene and air were fed through the catalytic reactor to give the desired contact time. The conditions and results of these experiments are shown in the Table. The percent per pass conversions are the gram-atoms of the carbon in the product specified which are found in the effluent of the reactor times 100, divided by the gram-atoms of carbon fed as ortho-xylene.

The active catalytic ingredients were ground to a powder. Separately, the appropriate mesh size Alundum particles were wetted with water so that the increase in weight over the dry particles was about 2 to 4%. There was no surface wetness on the Alundum. This material was rotated in an inclined glass jar, and the appropriate gram portions of the active catalytic ingredients were added. Essentially all of each portion of the active catalytic material was used up prior to the addition of the next portion. The catalysts were dried overnight at 110° C, and activated in the reactor for two hours at 426° C.

The catalysts for the reactions shown were prepared as follows:

EXAMPLE 1

20.6% ($Sb_2B_3V_{12}O_x + W_{1.32}$) and 79.4% Alundum 181.9 grams of vanadium pentoxide was slurried in about one liter of water. To this stirred slurry was added 40.4 grams of tungsten metal powder. The slurry was allowed to boil and reflux for several hours, during which time the color changed to deep blue-black.

An aliquot of this dark-colored slurry, containing 0.507 gram atom vanadium was transferred to another beaker. To this was added 7.84 grams of boric acid. This mixture was allowed to reflux for several hours. Finally, 12.3 grams of antimony trioxide was added and refluxing continued for several more hours. The final mixture was then evaporated to a thick paste and then dried overnight at a temperature of 110° C.

The black powder obtained was coated onto an Alundum support (10–30 mesh size) by the following procedure. 25 grams of Norton SA 203 Alundum was wetted with 2 grams of water by rolling in a round glass jar. The material was free-flowing and outwardly dry. To this material, in a rotating jar, was added 12.5 grams of the dried black powder in several incremental additions. The powder was evenly coated onto the surface of the Alundum. The final product was dried, and 6 grams of active powder was recovered such that the final product consisted of 6.5 grams of active powder and 25 grams of Alundum which calculated to be 20.6% active and 79.4% Alundum support.

EXAMPLES 2 AND 3

9.7% ($Sb_2B_3V_{12}O_x + W^{\circ 0.6}$) and 90.3% Alundum

In a manner essentially identical to that of Example 1, a similar catalyst was prepared with the following quantities of materials: 90.95 grams vanadium pentoxide, 9.2 grams of tungsten metal powder, 15.46 grams of boric acid, and 24.3 grams of antimony trioxide. The final slurry was evaporated to a thick paste and dried as before.

This powder, screened to less than 50 mesh, was coated onto 10–30 mesh Alundum in an analagous manner. After drying 9.8 grams of loose powder was removed such that the composition of the finished material was 9.7% active coating and 90.3% Alundum support.

EXAMPLES 4 AND 5

5% ($6B_3V_{12}O_x.94TiO_2$) and 95% Alundum 90.95 grams of vanadium pentoxide was slurried in 600 ml. of distilled water, and to this was added 9.7 grams of 85% hydrazine hydrate. The slurry starting darkening in color immediately. The slurry was refluxed for several hours. After this, 15.46 grams of boric acid was added and refluxing continued for several additional hours. Color changed from deep blue-black to dark green. This mixture was designated Mixture A.

An aliquot of Mixture A was removed such that the aliquot contained the equivalent of 6.26 grams of vanadium pentoxide. The aliquot was diluted to 350 ml. with distilled water and 97 grams of titanium dioxide was added. This slurry was refluxed for one hour then allowed to evaporate to a thick paste, which was then dried overnight at 110° C.

The dried product above was screened through 50 mesh then coated as follows: 30 grams of low porosity Norton BA 307 Alundum chips (10–20 mesh) was pre-wet with 0.5 grams of water in a rotating round glass jar. The material was free-flowing and outwardly dry in appearance. To this was added three portions, consisting of 0.53 grams each, of the catalytically active powder. The powder coated the Alundum uniformly. The coated material was dried overnight at 110° C. Final composition was 5% active component-95% Alundum support.

EXAMPLES 6 AND 7

5% ($6Sb_2B_3V_{12}O_x.94TiO_2$) and 95% Alundum

To the remaining portion of Mixture A having a calculated quantity of vanadium of 0.93 gram-atom was added 22.6 grams of antimony trioxide and the mixture was refluxed for two hours. This mixture was then designated Mixture B.

An aliquot of Mixture B was removed with a calculated amount of vanadium, calculated as vanadium pentoxide, equal to 5.57 grams. This aliquot was diluted to approximately 350 ml. with distilled water and 87.2 grams of titanium dioxide was added. The resulting slurry was stirred and then evaporated down to a thick paste, which was then dried overnight at 110° C. The dried material was crushed and screened through 50 mesh.

This dried material was coated onto 10–20 mesh low porosity Norton BA 307 Alundum chips in a manner analagous to that described above. 30 grams of Alundum was used, and this was pre-wet with 1.1 grams of water. Total amount of dried active material coated amounted to 1.59 grams, added in three equal increments. The finished material consisted of 5% active coating and 95% Alundum support.

EXAMPLE 8

8% ($Sb_2B_3V_{13}O_x$) and 92% Alundum

A portion of Mixture B was stirred and evaporated down to a thick paste and dried overnight at 110° C. The dried material was ground and screened through 50 mesh. This material was coated onto low porosity Norton BA 307 Alundum particles (10–20 mesh) in a manner analagous to that described above. 30 grams of Alundum was used and this was pre-wet with 1.2 grams of water. Five portions of active powder, consisting of 0.53 grams each, were added during the coating operation. The coated material resulting was dried overnight at 110° C. The coating was uniform with only a small amount of loose powder, thus the final composition was about 8% active coating and 92% Alundum support.

EXAMPLE 9

5% ($6Sb_2B_3V_{12}O_x.94ZrO_2/CaO$) and 95% Alundum

An aliquot of Mixture B containing 5.57 grams of vanadium pentoxide was diluted to about 300 ml. with distilled water. To this was added a powdered calcium oxide stabilized zirconia and the resulting slurry was well stirred and evaporated down to a thick paste. This was dried overnight at 110° C. and then ground and screened through 50 mesh.

This material was coated using 30 grams of low porosity Norton BA 307 Alundum which has been pre-wet with 1.0 gram of water. Three 0.53 portions of the active catalytic powder was coated onto the Alundum. The material was dried at 110° C. and consisted of 5% of the active powder and 95% Alundum support.

EXAMPLE 10

5% ($6Sb_2B_3V_{12}O_x.94SiO_2$) and 95% Alundum

An aliquot of Mixture B containing 5.57 grams of vanadium pentoxide was diluted to about 300 ml. with water. To this was added 87.2 grams of Illinois Mineral, type 1160 amorphous diatomaceous silica powder. The slurry was stirred and evaporated down to a thick paste. This was dried overnight at 110° C. and then ground and screened through 50 mesh.

This material was coated onto 10–20 mesh low porosity Alundum in the same manner as described in Example 6. The finished product consisted of 5% powder in the coating and 95% Alundum support.

EXAMPLE 11

5% ($6V_2O_5.94TiO_2$) and 95% Alundum 6 grams of vanadium pentoxide was slurried in 200 ml. of distilled water. To this was added 0.64 gram of 85% hydrazine hydrate. The brown suspension turned color to dark green and then black. The slurry was stirred and refluxed for 2 hours. The slurry was then diluted to about 400 ml. with distilled water and 94 grams of powdered titanium dioxide (anatase) was added. This slurry was stirred and heated under reflux for about an hour then allowed to evaporate to a thick paste. This material was dried at 110° C. for 3 hours and a portion was ground and screened through 60 mesh for the coating procedure.

30 grams of low porosity Norton BA 307 Alundum (10–20 mesh) was soaked in distilled water for ten minutes and then dried on a paper towel. The water pickup amounted to 1.2 grams. The Alundum appeared moist and sticky so it was carefully dired with a stream of air until the water content was reduced to 0.6 gram. It was then free flowing and outwardly dry.

In a rotating round glass jar, the Alundum was coated with the above powder which was added in three separate increments of 0.53 grams each. The final product was dried at 110° C. The coating was uniform with a somewhat powdery surface. It consisted of 5% active material in the coating and 95% Alundum support.

In the same manner as described in the examples above, other reactant ratios can be employed; for example air and ortho-xylene in a ratio of 50/1 could be fed over a catalyst at a pressure of 2 atmospheres and a temperature of 325° C. to obtain desirable yields of phthalic anhydride.

Also in the same manner as shown for the catalysts above, other catalysts of the invention, such as 5% ($10Cu_2Fe_{0.1}B_3V_{12}x.90TiO_2$) and 95% titania spheres, 30% ($2CoMo_2V_{12}O_x.98TiO_x$) and 70% silica spheres and 10% ($15Ni_2MnW_{0.5}Sb_5V_{12}O_x.85SiO_2$) and 90% alumina spheres could be employed as the catalyts of the invention to obtain the especially desirable results of the invention.

Table

Oxidation of Ortho-Xylene to Phthalic Anhydride

| Ex. | Catalyst | %V | Temp., ° C. Bath | Temp., ° C. Exotherm | Air/ Xylene | C.T. Sec. | Per Pass Conversion, % Phthalic Anhydride | Per Pass Conversion, % Maleic Anhydride |
|-----|----------|-----|------|----------|--------|------|-----------|----------|
| 1 | 20.6% ($Sb_2B_3V_{12}O_x+W°_{1.32}$) and 79.4% Alundum | 6.95 | 357 | 377 | 69 | 1.1 | 35.4 | 8.7 |
| 2 | 9.7% ($Sb_2B_3V_{12}O_x+W°_{0.6}$) and 90.3% Alundum | 3.53 | 372 | 385 | 69 | 1.1 | 45.8 | 3.8 |
| 3 | " | " | 385 | 472 | 69 | 1.0 | 43.8 | 9.7 |
| 4 | 5% ($6B_3V_{12}O_x.94TiO_2$) and 95% Alundum | 0.14 | 399 | 426 | 69 | 1.0 | 66.3 | 5.2 |
| 5 | " | " | 399 | 419 | 100 | 1.0 | 73.8 | 5.3 |
| 6 | 5% ($6Sb_2B_3V_{12}O_2.94TiO_2$) and 95% Alundum | 0.12 | 399 | 417 | 100 | 1.0 | 75.0 | 6.6 |
| 7 | " | " | 385 | 393 | 100 | 1.0 | 77.7 | 4.4 |
| 8 | 8% ($Sb_2B_3V_{12}O_x$) and 92% Alundum | 3.12 | 399 | 459 | 100 | 1.0 | 47.2 | 10.5 |
| 9 | 5% ($6Sb_2B_3V_{12}O_x.94ZrO_2/CaO$) and 95% Alundum | 0.12 | 455 | 472 | 100 | 1.0 | 58.8* | |
| 10 | 5% ($6Sb_2B_3V_{12}O_x.94SiO_2$) and 95% Alundum | " | 427 | 443 | 100 | 1.0 | 66.8 | 4.9 |
| 11 | 5% ($6V_2O_5.94TiO_2$) and 95% Alundum | 0.17 | 399 | 416 | 100 | 1.0 | 64.1 | 7.1 |

*Measured as total acid

We claim:

1. In the process for preparing phthalic anhydride by contacting a mixture of ortho-xylene and molecular oxygen at a temperature of about 200° C to about 600° C in the presence of an oxidation catalyst which is useful for reaction in a fixed-bed reactor, the improvement comprising:

using an oxidation catalyst consisting of
a. an essentially inert, porous support having a particle size of at least 20 microns, said inert support having an outer surface; and
b. a coating of a catalytically active material on said outer surface of said support which strongly adheres to said outer surface of said inert support, wherein said catalytically active material contains:

$$A_aD_bV_{12}O_x$$

wherein
A is Fe, Cr, Ni, Co, Mn, Cu, Ag, Bi, Zn, Mo, W or mixture thereof;
D is B, Sb or mixture thereof;
$a$ is a number from greater than 0 to 5;
$b$ is a number from greater than 0 to 10; and
$x$ is the number of oxygens required to satisfy the valence requirements of the other elements present; wherein the weight of vanadium is less than 10% of the total weight of the oxidation catalyst.

2. The process of claim 1 wherein A is a metal selected from molybdenum or tungsten.

3. The process of claim 1 wherein A is tungsten metal and D is a mixture of antimony and boron.

4. The process of claim 1 wherein D is a mixture of antimony and boron.

5. The process of claim 1 wherein b is a number from greater than 0 to 5.

6. The process of claim 1 wherein the inert support has a particle size of about 0.2 cm. to about 2 cm.

7. The process of claim 1 wherein the reaction is conducted at a temperature of about 300° to about 500° C.

8. The process of claim 1 wherein the catalyst is prepared by (a) contacting the inert support with a measured amount of a liquid to produce a partially wet support, said support being one that does not have the appearance of having liquid on the outer surface of the support, but has at least some liquid absorbed on the support, and (b) rolling said support in a powder of the catalytically active material to produce a support having a uniform coating of the catalytically active material on the outer surface of said support.

9. In the process for preparing phthalic anhydride by contacting a mixture of ortho-xylene and molecular oxygen at a temperature of about 200° C to about 600° C in the presence of an oxidation catalyst which is useful for reaction in a fixed-bed reactor, the improvement comprising:

using an oxidation catalyst consisting of:
  a. an essentially inert, porous support having a particle size of at least 20 microns, wherein said support has an outer surface and wherein said support is capable of absorbing at least 1% by weight water based upon the weight of the support, but does not have the appearance of having water on the outer surface of the support;
  b. a coating of a catalytically active oxide material and a titanium dioxide support material on said outer surface of said inert support which strongly adheres to said outer surface of said inert support, wherein said catalytically active oxide material contains a mixture of boron, antimony, and an oxide of vanadium such that the weight of vanadium is less than 10% of the total weight of the oxidaton catalyst.

10. The process of claim 9 wherein the support absorbs from 2% to 4% by weight water based on the weight of the support.

11. The process of claim 9 wherein the catalyst contains less than about 5% by weight of vanadium.

12. The process of claim 9 wherein the catalyst contains less than about 1% by weight of vanadium.

13. The process of claim 9 wherein the catalyst contains less than about 0.5% by weight of vanadium.

14. The process of claim 9 wherein the catalyst is prepared by (1) contacting the inert support with a measured amount of liquid to produce a partially wet support, said support being one that does not have the appearance of having liquid on the outer surface of the support, but has at least some liquid absorbed on the support, and (2) rolling said support in a powder of the catalytically active material to produce a support having a uniform coating of the catalytically active material on the outer surface of said support.

15. In the process of preparing phthalic anhydride by contacting a mixture of ortho-xylene and molecular oxygen at a temperature of about 200° C to about 600° C in the presence of an oxidation catalyst which is useful for reaction in a fixed-bed reactor, the improvement comprising:

using an oxidation catalyst consisting of
using an oxidation catalyst consisting of
  a. an essentially inert, porous support having a particle size of at least 20 microns, said inert support having an outer surface; and
  b. a coating of a catalytically active oxide material and a titanium dioxide support material on said outer surface of said inert support which strongly adheres to said outer surface of said inert support, said catalytically active material containing boron, and an oxide of vanadium, such that the weight of vanadium is less than 10% of the total weight of the oxidation catalyst.

16. The process of claim 15 wherein the catalyst contains less than about 0.5% by weight of vanadium.

17. The process of claim 15 wherein the catalyst is prepared by (1) contacting the inert support with a measured amount of liquid to produce a partially wet support, said support being one that does not have the appearance of having liquid on the outer surface of the support, but has at least some liquid absorbed on the support, and (2) rolling said support in a powder of the catalytically active material to produce a support having a uniform coating of the catalytically active material on the outer surface of said support.

* * * * *